United States Patent
Kwun et al.

(10) Patent No.: US 7,852,073 B2
(45) Date of Patent: *Dec. 14, 2010

(54) METHOD AND DEVICE FOR LONG-RANGE TORSIONAL GUIDED-WAVE INSPECTION OF PIPING WITH A PARTIAL EXCITATION AND DETECTION AROUND THE PIPE CIRCUMFERENCE

(75) Inventors: Hegeon Kwun, San Antonio, TX (US); Hirotoshi Matsumoto, Nagasaki (JP); James F. Crane, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 218 days.

This patent is subject to a terminal disclaimer.

(21) Appl. No.: 11/823,113

(22) Filed: Jun. 25, 2007

(65) Prior Publication Data
US 2008/0315872 A1   Dec. 25, 2008

(51) Int. Cl.
G01N 27/82   (2006.01)
(52) U.S. Cl. .................... 324/262; 324/238
(58) Field of Classification Search ............ None
See application file for complete search history.

(56) References Cited
U.S. PATENT DOCUMENTS

| | | |
|---|---|---|
| 3,170,114 A | 2/1965 | Placke |
| 3,568,049 A | 3/1971 | Barton |

(Continued)

FOREIGN PATENT DOCUMENTS

JP    07253365 A  * 10/1995

OTHER PUBLICATIONS

Kwun, Hegeon, Light, Glenn, "Magnetostrictive sensor technology proven in process applications", Oil & Gas Journal, May 22, 2000, Process Plant Maintenance; p. 77, PennWell Publishing Company.

(Continued)

*Primary Examiner*—Jay M Patidar
(74) *Attorney, Agent, or Firm*—Kammer Browning PLLC

(57) ABSTRACT

Sensor assemblies and methods are described that facilitate the use of a long-range torsional guided-wave inspection system for inspecting pipes, tubes, or other longitudinal cylindrical structures, with a partial excitation and detection around the pipe circumference. The sensor assemblies comprise a plate-type magnetostrictive sensor probe positioned beneath a compressible/expandable bladder and an inverted U-shaped frame that retain and position the sensor probe against the external wall of the pipe under inspection. Preferably, a magnetostrictive strip is positioned in direct contact with the pipe wall over which the plate magnetostrictive sensor probe is positioned. The probe is preferably curved to match the curvature of the external surface of the pipe. A pad may be positioned between the probe and the magnetostrictive strip to improve compliance with irregular pipe surfaces. The frame (and therefore the sensor assembly) is held in place by a belt that encircles the pipe and may be tensioned in order to pull the frame against the pipe, and through the compressive force associated with the bladder, direct the magnetostrictive sensor probe against the surface of the pipe or against the magnetostrictive strip positioned on the surface of the pipe. Methods are described for placement of the magnetostrictive strip and the positioning of the magnetostrictive sensor probe.

15 Claims, 5 Drawing Sheets

U.S. PATENT DOCUMENTS

| | | | |
|---|---|---|---|
| 4,510,447 A | | 4/1985 | Moyer |
| 4,543,528 A | | 9/1985 | Baraona |
| 4,784,762 A | | 11/1988 | Taliaferro |
| 4,916,394 A | | 4/1990 | Thompson |
| 5,479,099 A | * | 12/1995 | Jiles et al. ............... 324/235 |
| 5,841,277 A | * | 11/1998 | Hedengren et al. ......... 324/240 |
| 6,373,245 B1 | * | 4/2002 | Kwun et al. .............. 324/240 |
| 6,373,252 B1 | | 4/2002 | Eslambolchi et al. |
| 6,812,707 B2 | | 11/2004 | Yonezawa et al. |
| 6,968,727 B2 | * | 11/2005 | Kwun et al. ............... 73/1.82 |
| 7,100,462 B2 | * | 9/2006 | Gronvall .................. 73/866.5 |
| 2001/0022514 A1 | * | 9/2001 | Light et al. ............... 324/240 |
| 2007/0090904 A1 | * | 4/2007 | Kim et al. ................ 335/205 |

OTHER PUBLICATIONS

3P Services GmbH & Co., "Unit detects internal pipeline corrosion", Oil & Gas Journal, Mar. 6, 1995, Equipment/Software/Lit; p. 78, PennWell Publishing Company.

Phair, Matthew, "Technology Plays a Key Role in Keeping Pipeline Network Fit", Engineering News-Record, Jan. 29, 2001, Pipelines; vol. 246; No. 4; p. 60, McGraw-Hill Companies, Inc.

* cited by examiner

METHOD AND DEVICE FOR LONG-RANGE TORSIONAL GUIDED-WAVE INSPECTION OF PIPING WITH A PARTIAL EXCITATION AND DETECTION AROUND THE PIPE CIRCUMFERENCE

BACKGROUND OF THE INVENTION

1. Field of the Invention

The present invention relates generally to methods and systems for non-destructive testing and inspection of pipes, tubes, and other longitudinal cylindrical structures. The present invention relates more specifically to methods and systems for accurately positioning long-range torsional guided-wave inspection sensors on pipes, tubes, and other cylindrical structures to create partial excitation and detection around the pipe circumference.

2. Description of the Related Art

Long-range, guided-wave inspection technology is an emerging technology that has the capability of quickly surveying a large volume of a structure for defects and providing comprehensive condition information on the integrity of the structure. Using relatively low-frequency (typically under 100 kHz) guided-waves in the pulse-echo testing mode, this technology performs a 100% volumetric examination of a large area of a structure and detects and locates internal and external defects in the area around a given test position. In above-ground pipelines, for example, a test range of more than 500 feet can be achieved in one direction for detecting 2% to 3% defects from a given test position. In this case, percent refers to the circumferential cross-sectional area of the defect relative to the total pipewall cross section. This guided-wave inspection technology, including the magnetostrictive sensor (MsS) technology developed at Southwest Research Institute in San Antonio, Tex., is now widely used for testing piping networks in processing plants such as refineries and chemical plants. The preferred guided-wave mode for piping inspection is the torsional (T) wave.

For piping inspections, guided-wave probes that encircle the entire pipe circumference are presently in use. To install a guided-wave probe for piping inspection, the basic systems and methodologies require full access around the pipe circumference with about 3 to 5 inches of spacing. When access is limited to only a portion of the piping circumference, the long-range guided-wave inspection method is difficult to apply. Examples of limited access include pipelines placed very close to a wall and pipes or tubes placed closely together (such as with superheater and reheater tubes in boilers).

Examples of efforts that have been made in the past to provide systems and methods for positioning sensors in connection with the inspection of longitudinal cylindrical structures such as pipes and tubes include those disclosed in the following U.S. patents:

U.S. Pat. No. 4,916,394 issued to Thompson on Apr. 10, 1990 entitled Device for Adjustable Mounting of Magnetic Sensing Coils Used in Pipe Inspection describes a mounting shoe and a pair of adjustable contact wedges that may be moved in and out to accommodate the curvature of a pipe under inspection. The magnetic sensing coils in this case are protected by a shim that positions the coils in an optimum sensing range from the surface of the pipe.

U.S. Pat. No. 4,543,528 issued to Baraona on Sep. 24, 1985 entitled Flexible Probe Assembly for Use in Non-Destructive Testing of a Convex Workpiece Surface describes a complicated frame structure that includes a flexible array of sensor heads that are arranged in tension to conform to the pipe when directed against its convex surface. Multiple sensor heads are required in order to provide compliance with the curved surface of the pipe.

U.S. Pat. No. 6,373,252 issued to Eslambolchi et al. on Apr. 16, 2002 entitled Method and Apparatus Locating a Cable in a Pipe describes a system and method for locating a cable within the confines of a cylindrical pipe. In this case, the sensor placed in contact with the pipe is configured with an arcuate bottom surface that matches the curvature of the exterior circumference of the pipe. No specific mechanism is described for urging the curved surface of the detector head against the convex pipe surface.

U.S. Pat. No. 4,784,762 issued to Taliaferro entitled Magnetic Trap describes a method for positioning a Hall effect sensor on the external surface of a cylindrical pipe. The structure includes a magnetic trap positioned in conjunction with a magnetically transparent sheet on one side of which a magnet is mounted to produce a magnetic field. The Hall effect sensor is positioned adjacent the magnet to sense the magnetic field.

U.S. Pat. No. 3,568,049 issued to Barton on Mar. 2, 1971 entitled Adjustable Search Shoe for Use in Non-Destructing Testing of Tubular Members describes a sensor structure that includes an object engaging surface that may be mechanically adjusted to change its curvature so as to conform to the wall of the pipe or tubular object under inspection.

U.S. Pat. No. 5,841,277 issued to Hedengren et al. on Nov. 24, 1998 entitled Hand-Holdable Probe Having a Flexible Eddy Current Sensor describes a hand-held probe incorporating an eddy current sensor that can be moved across the surface being tested. The device is not specifically directed towards curved structures such as pipes or tubes, but instead describes a sensor with a generally planar bottom surface that has flexible or resilient characteristics. A primary objective of this device is to maintain an optimal standoff distance through the use of a flexible sensor/surface interface.

U.S. Pat. No. 4,510,447 issued to Moyer on Apr. 9, 1985 entitled Inspection Apparatus for Electro Magnetically Detecting Flaws in the Wall of the Pipe describes a large, complex structure that incorporates a moveable frame having a sensor urged against the surface of a pipe with a spring. The overall structure is a sensor assembly that establishes a closed magnetic circuit to generate a fluctuating magnetic field axially through the wall of the pipe between the poles of the electromagnet.

U.S. Pat. No. 6,812,707 issued to Yonezawa et al. on Nov. 2, 2004 entitled Detection Element for Objects and Detection Device Using the Same describes a sensor structure that includes a V-shaped engagement channel on a sensor head that incorporates an antenna coil wound around a magnetic member. The V-shaped channel facilitates positioning and placement of the sensor against the curved outer circumference of a pipe or tube.

U.S. Pat. No. 5,479,099 issued to Jiles et al. on Dec. 26, 1995 entitled Magnetic Inspection Heads Suited for Contoured or Irregular Surfaces describes an arrangement of coils associated with an array of moveable pins within an assembly that is positioned against the curved surface of a pipe or tube. The pins adjust their position according to contact with the external circumference of the pipe and thereby establish a conformed contact surface for the sensor on the magnetic inspection head.

In general, the prior efforts in the field have been directed to partial circumference sensor structures only where the type of interrogating signal is easily suited to such configurations. That is, none of the previous efforts at partial circumferential orientation have provided suitable sensor adherence structures for use in conjunction with long-rang torsional guided-waves. These interrogating waves have heretofore been limited to propagation from sensor structures that circumferentially surround the pipe or tube. No sensor structures have been designed that can take advantage of the volumetric inspection capabilities of long-range guided-waves where access to the entire circumference of the pipe or tube is restricted. It would be desirable, therefore to have a sensor structure, and a method for its implementation, that overcomes many of the problems of existing sensor structures and the requirement that they fully encircle the pipe or tube under inspection.

In the present invention, systems and methods for inspecting piping with limited access using partial excitation/detection around the pipe circumference are described. The systems and methods are built upon existing magnetostrictive sensor (MsS) methods and devices, particularly the thin magnetostrictive strip approach (described in U.S. Pat. No. 6,396,262, entitled Method and Apparatus for Short Term Inspection or Long Term Structural Health Monitoring; U.S. Pat. No. 6,429,650, entitled Method and Apparatus Generating and Detecting Torsional Wave Inspection of Pipes and Tubes; and U.S. Pat. No. 6,917,196, also entitled Method and Apparatus Generating and Detecting Torsional Wave Inspection of Pipes and Tubes, the disclosures of which are each incorporated herein in their entirety by reference) and the plate MsS probe (described in U.S. Pat. No. 6,294,912, entitled Method and Apparatus for Nondestructive Inspection of Plate Type Ferromagnetic Structures using Magnetostrictive Techniques, the disclosure of which is incorporated herein in its entirety by reference), but modified to fit the purposes of the present invention.

SUMMARY OF THE INVENTION

The present invention therefore describes systems and methods that facilitate the use of a long-range torsional guided-wave inspection system for inspecting pipes, tubes, or other longitudinal cylindrical structures, with partial excitation and detection around the pipe circumference. The sensor assembly comprises a plate-type magnetostrictive sensor probe positioned beneath a compressible/expandable bladder and an inverted U-shaped frame that retains and positions the sensor probe against the external wall of the pipe under inspection. Preferably (as necessary), a magnetostrictive strip is positioned in direct adhesion to the pipe wall over which the plate magnetostrictive sensor probe is positioned. The probe is preferably curved to match the curvature of the external surface of the pipe. A pad may be positioned between the probe and the magnetostrictive strip to improve sensor performance by adapting to irregularities in the surface. The frame is held in place by a belt that encircles the pipe. The belt may be tensioned by a buckle or other belt tensioning device in order to pull the frame firmly against the pipe. The compressive force derived from internal pressures within the bladder directs the magnetostrictive sensor probe against the surface of the pipe, or more specifically, against the magnetostrictive strip positioned on the surface of the pipe. Methods are described for placement of the magnetostrictive strip and the placement and positioning of the magnetostrictive sensor probe with its supporting frame.

A preferred method for inspecting piping with limited access using a partial excitation/detection around the pipe circumference is as follows:

(1) First, a thin magnetostrictive strip (preferred material is the iron cobalt alloy disclosed in U.S. Pat. No. 6,917,196 referenced above) is positioned on the pipe under inspection along the pipe circumference. To minimize the generation of unwanted extraneous signals, the length of the strip is preferably about four times the T (torsional wave) wavelength at the operating frequency or approximately equal to one-half of the pipe circumference, whichever is shorter. When the length of the strip is less than the above, the quality of data will be degraded due to the generation of unwanted signals. That is, the shorter the strip length, the greater the degradation. The width of the strip should be the same as, or slightly larger than, the width of the plate MsS probe being used (described in detail below). The magnetostrictive strip can be attached to the pipe by bonding with an adhesive (such as epoxy), using double-sided adhesive tape, or by simply applying pressure to the strip for mechanical coupling. The strip is magnetized along the lengthwise direction for T-wave MsS operation (as disclosed in U.S. Pat. No. 6,429,650 referenced above).

(2) A curved MsS probe is then placed over the thin magnetostrictive strip in position on the pipe surface. The plate MsS probe is either a core type (such as disclosed in U.S. Pat. No. 6,294,912 referenced above) or a flat coil type (such as disclosed in U.S. Pat. No. 6,396,262 also referenced above). A frame and attachment belt may be provided to secure the MsS probe to the pipe. The band or belt is tensioned sufficiently to keep the frame against the pipe and the magnetostrictive strip pressed against the pipe. This is further facilitated by the use of an elastic or air-operated bladder to achieve close contact and good mechanical coupling between the magnetostrictive strip and the plate MsS probe assembly, and to evenly distribute the pressure on the strip.

(3) Finally, the MsS probe is connected to MsS instrumentation as is known in the art. The system thus configured may be used to generate interrogating signals into the pipe and acquire relevant inspection data from return signals within the pipe. Further features of both the system of the present invention and its method of use will become apparent from the following detailed description with reference to the appended drawing figures.

BRIEF DESCRIPTION OF THE DRAWINGS

The accompanying figures will give a fuller description and a better understanding of the details and advantages of the present invention. The drawing figures appended may be briefly described as follows.

DETAILED DESCRIPTION OF THE PREFERRED EMBODIMENTS

Figure 1:
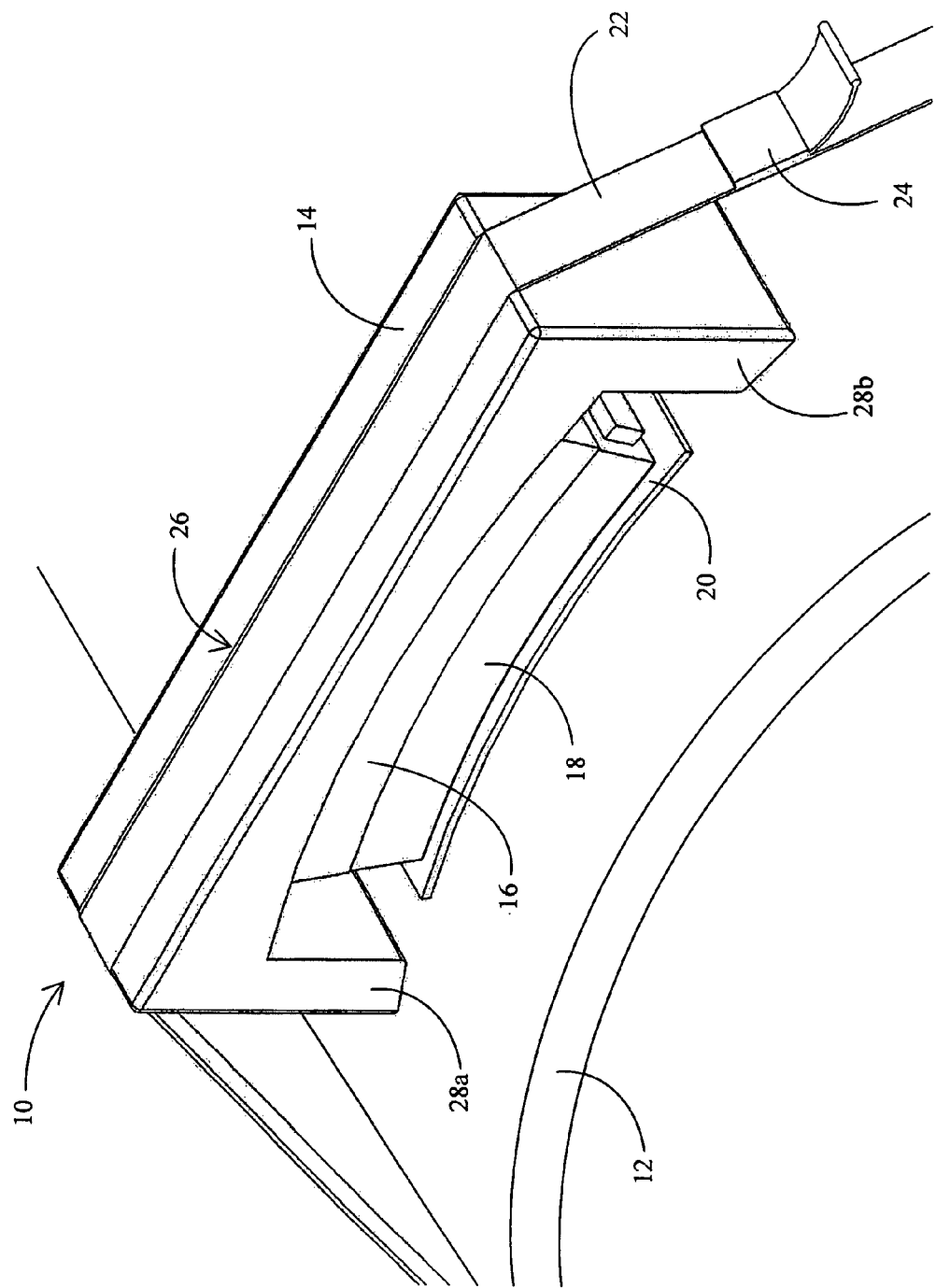
FIG. 1 is a perspective view of the sensor assembly of the present invention positioned in conjunction with the external surface of a cylindrical pipe structure.

Reference is made first to FIG. 1 for a brief description of the overall plate magnetostrictive sensor (MsS) assembly of the present invention positioned as it would normally be placed in conjunction with the external curved surface of a cylindrical pipe or tube. Plate magnetostrictive sensor (MsS) assembly 10 is positioned on the external curved surface of pipe 12 and encompasses a radial portion of the entire circumference of the pipe. Assembly 10 is primarily comprised of a inverted U-shaped frame 14 held in place by belt 22 that encircles the pipe 12. Belt 22 is tensioned by buckle tensioning device 24 in a manner that secures the sensor assembly firmly against the external surface of the pipe. Belt 22 is maintained on frame 14 within belt slot 26 which is a channel depression that prevents belt 22 from slipping off of frame 14 while under tension or while the sensor assembly is being positioned into place.

A plate magnetostrictive sensor probe 18 is positioned on top of pad 20, which itself is positioned over magnetostrictive strip (not shown in this view) that is positioned on and/or adhered to the external surface of pipe 12. Between plate magnetostrictive sensor probe 18 and frame 14 is bladder/elastomeric material 16 that serves to cushion the attachment of the sensor and provide an engaging force downward onto the external surface of pipe 12. This downward force is limited by the orientation and length of frame foot 28a and frame foot 28b, which form the arms of the inverted U-shaped frame 14. In this manner tensioning of belt 22 forces frame 14 downward onto the external surface of pipe 12 to a point that is limited by the extent of frame feet 28a and 28b. The bladder/elastomeric material 16 maintains the pressure/force necessary to maintain compliance of the plate magnetostrictive sensor probe in close proximity to the magnetostrictive strip positioned on the pipe's surface. The thickness of pad 20 provides the optimal positioning distance between the sensor probe 18 and the magnetostrictive strip (not shown) and also serves to further cushion the placement of the assembly against the sometimes irregular surface of the pipe.

Figure 2:
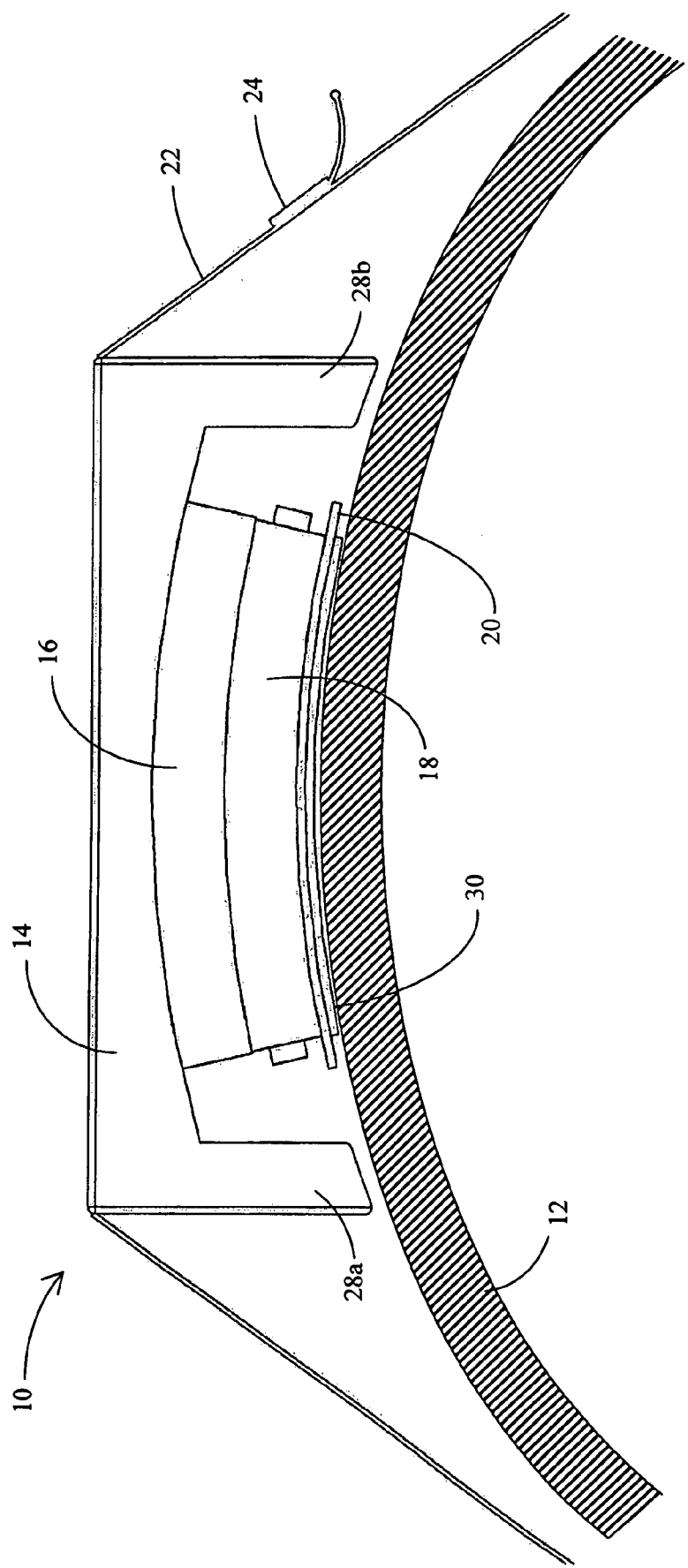
FIG. 2 is a side-plan view of the sensor assembly of the present invention positioned on a cylindrical structure prior to being tensioned into place.

Reference is now made to FIG. 2 for a clearer description of the manner in which the magnetostrictive strip is positioned beneath pad 20 in adherence to the external surface of pipe 12. The view in FIG. 2 is along the axis of the pipe or cylindrical structure and shows the manner in which frame 14 presses down against bladder/elastomeric material 16 to force plate magnetostrictive sensor probe 18 against pad 20 and thereby against magnetostrictive strip 30 onto pipe 12. Belt 22, by way of buckle tensioning device 24, pulls frame 14 into compliance with the curved surface of pipe 12, again limited by the length and position of frame feet 28a and 28b. When properly tensioned, feet 28a and 28b come into direct contact with the external surface of pipe 12 compressing bladder/elastomeric material 16 in a manner that causes it to exert an outward expansive force downward onto plate magnetostrictive sensor probe 18, thereby forcing it into compliance with pad 20 and magnetostrictive strip 30.

It should be noted that the curvature of pipe 12 determines in part the preferred curvature of plate magnetostrictive sensor probe 18 as well as the preferred configuration of frame 14 under which the sensor probe is positioned. Bladder/elastomeric material 16, on the other hand, is a flexible structure that follows and adapts to the curvature of frame 14 and plate magnetostrictive sensor probe 18 that together serve to compress the material. Magnetostrictive strip 30 is a flexible magnetostrictive material that is, as described above, adhered directly to the curved surface of pipe 12, as is pad 20 which conforms to the surface of pipe 12 covering magnetostrictive strip 30. Frame feet 28a and 28b each have angled end surfaces that come into contact with pipe 12 that likewise approximately follow the curved surface of the pipe.

Figure 3:
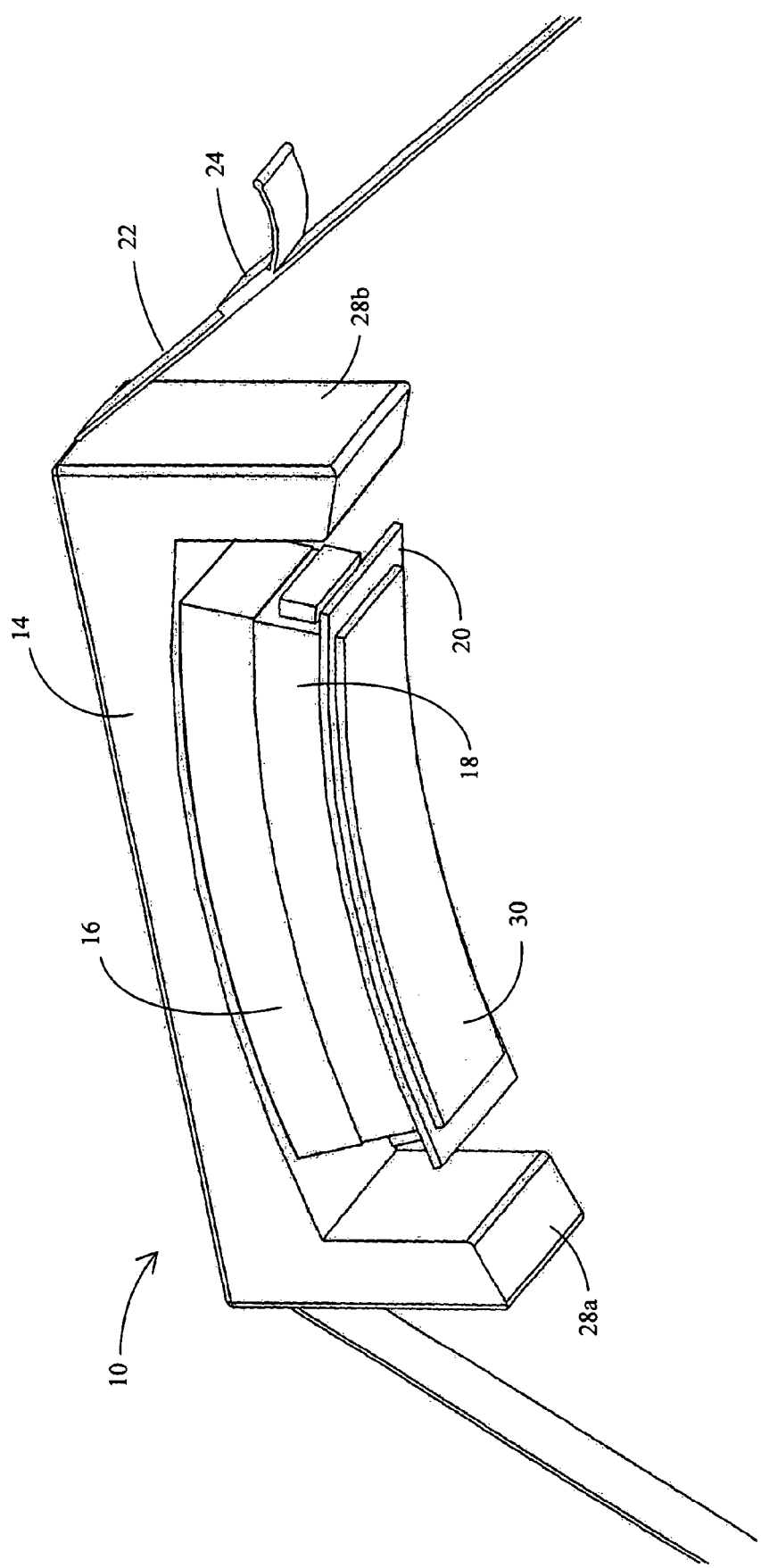
FIG. 3 is a perspective view of the sensor assembly of the present invention shown removed from a pipe structure, disclosing the details of the underside components of the assembly.

Reference is now made to FIG. 3 for a description of the plate magnetostrictive sensor assembly 10 removed from its position on the pipe in a manner that exposes the magnetostrictive strip 30 and its position on pad 20. In this view, the manner in which pad 20 covers magnetostrictive strip 30 in what would be its position on the pipe (now shown) can be more clearly seen. Plate magnetostrictive sensor probe 18 is positioned opposite magnetostrictive strip 30 on pad 20. Bladder/elastomeric material 16 is positioned on (and is preferably adhered to) curved plate magnetostrictive sensor probe 18. Frame 14 is positioned on (and preferably adhered to) bladder/elastomeric material 16 as described above. The curved or angled lower end surfaces of frame feet 28a and 28b are also seen in this view.

As indicated above, the structure of the present invention is intended to provide a means for securing a plate magnetostrictive sensor against the external surface of a cylindrical structure without the necessity of having access to the entire circumference of the pipe or tube. In many instances, it is impossible to place a magnetostrictive sensor probe, such as those described in the referenced patents, in conjunction with a pipe or tube that is rigidly held in place against a wall, in a trench, or tightly packed together with other parallel pipes or the like. The assembly of the present invention allows the use of only a portion of the exposed circumference of a pipe to position and place a plate magnetostrictive sensor probe.

Figure 4A:
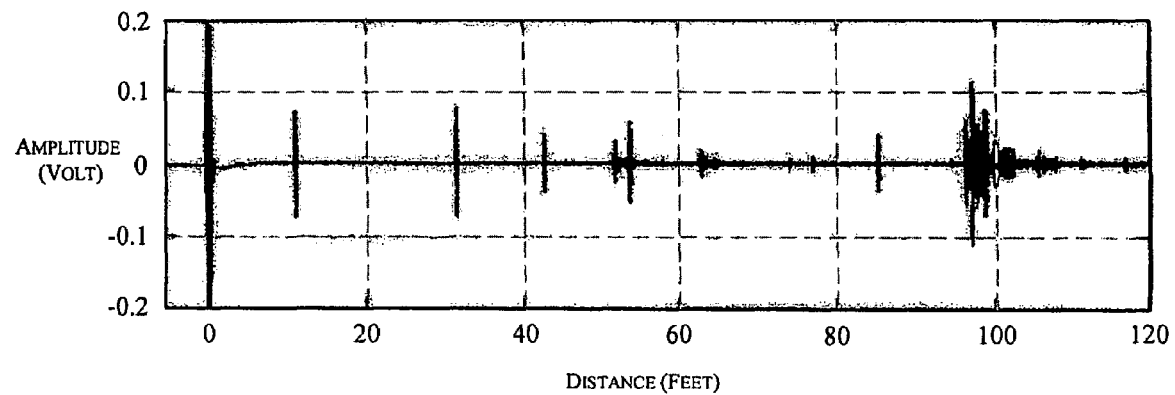
FIGS. 4A and 4B are signal plots comparing a sensor signal utilizing a system fully encircling a pipe with the system of the present invention only partially encircling the external surface circumference of the pipe.
Figure 4B:
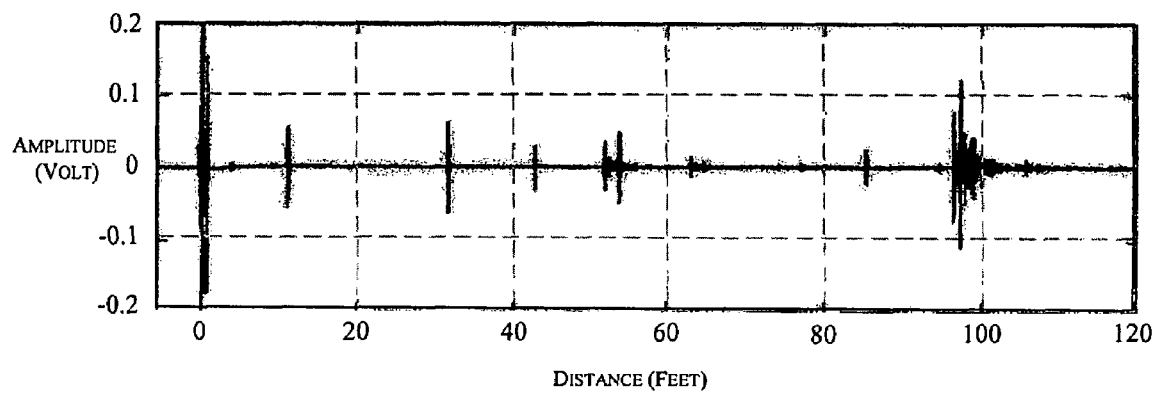

To illustrate the quality of data that can be obtained using the invented method, an example of data obtained from a 16 inch (OD) pipeline sample is given in FIGS. 4A and 4B. The plot in FIG. 4A is 64 kHz T-wave data obtained normally using a fully encircling MsS. The plot in FIG. 4B is the counterpart obtained using an 8 inch long, curved core-type plate MsS probe (the length is equal to 4 times the wavelength at 64 kHz). As shown in this example, the data obtained using the plate MsS probe were approximately the same as the data obtained using the fully encircling MsS.

Since it takes a period of time for the guided-wave generated by a local excitation to spread fully around the pipe circumference, the invented method has a blind area near the probe. The extent of the blind area depends on the pipe size and the probe length relative to the wavelength. This blind area, which is absent when a fully encircling MsS is used, is a minor trade-off of utilizing the local excitation approach of the present invention.

FIGS. 4A and 4B show the effectiveness of the sensor assembly of the present invention despite the fact that it does not completely encircle the pipe or tube. FIG. 4A shows the signal returned from a fully encircling magnetostrictive sensor assembly, while FIG. 4B discloses the same signal on the same pipe structure using the plate magnetostrictive sensor assembly of the present invention. Close adherence to the signal characteristics are disclosed in FIG. 4B to those signal characteristics shown in FIG. 4A.

Figure 5:
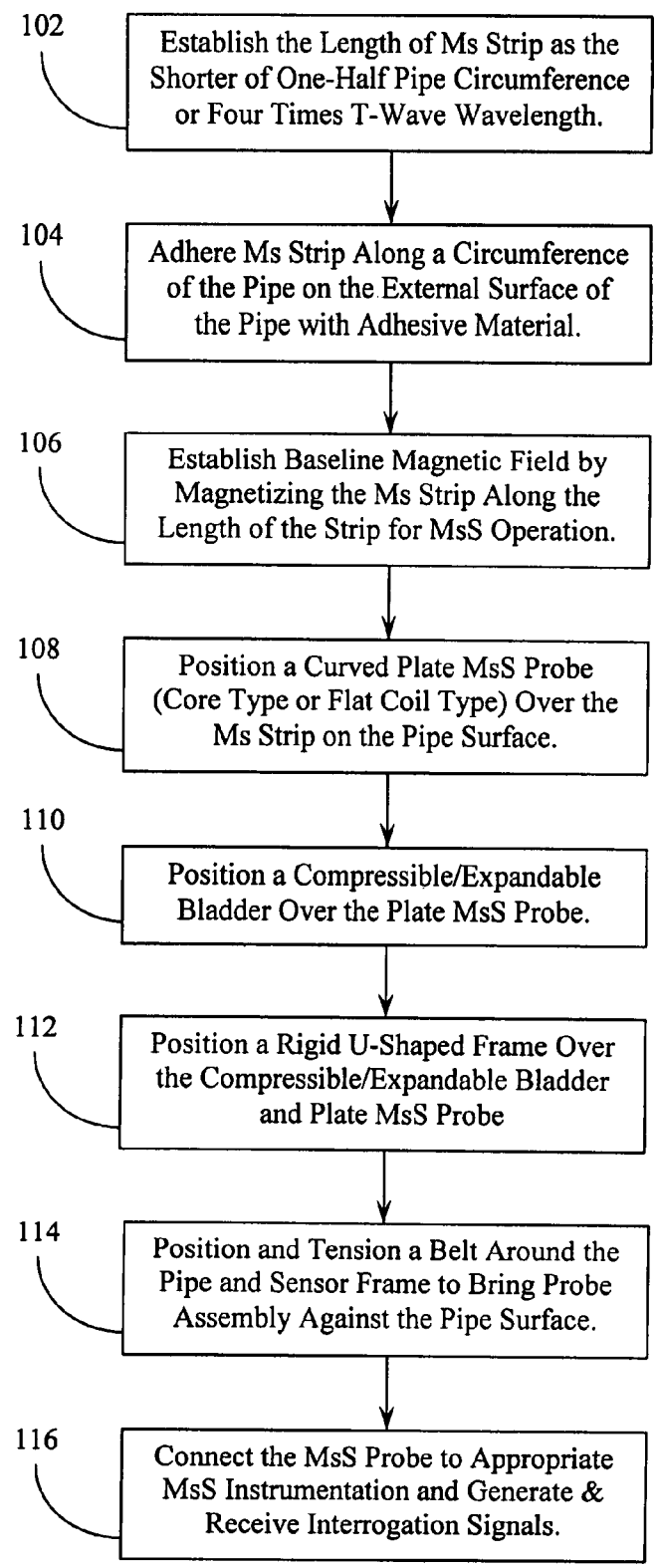
FIG. 5 is a flowchart showing the basic process steps associated with the methodology of implementing the system of the present invention.

Reference is now made to FIG. 5 for a brief description of the basic method steps associated with implementation of the system of the present invention. As indicated above, some variations in the methodology will result from structural variations in the configuration of the pipe under inspection. Specific types of magnetostrictive sensors may also determine some modification to the sequence of steps carried out. In general, however, the methodology of the present invention is reflected by the following process.

Initially, at Step 102, it is necessary to establish the length of the magnetostrictive strip as being the shorter of one-half the pipe circumference or four times the T-wave (torsional wave) wavelength. As indicated above, these dimensions minimize the generation of unwanted extraneous signals within the sensor. The width of the strip should be the same as or slightly larger than the width of the plate magnetostrictive sensor probe described above. Once the magnetostrictive strip has been configured, it is adhered, at Step 104 along a circumference of the pipe on the external surface of the pipe with adhesive material. As described above, the strip may be attached to the pipe by bonding with an adhesive such as epoxy or using some other form of double-sided adhesive material followed by the application of pressure to the strip to form a mechanical coupling with the outer surface of the pipe.

In order to establish a bias magnetic field, the magnetostrictive strip is magnetized at Step 106 along the length of the strip in order to optimize torsional wave magnetostrictive sensor operation. At Step 108 the curved plate magnetostrictive sensor probe is positioned over the magnetostrictive strip of material on the pipe surface. For a number of reasons, as described above, it is preferable to place a pad between the magnetostrictive strip of material and the curved plate magnetostrictive sensor probe. The probe itself may be either the core type (described above and in the referenced patents) or a flat coil type probe (also described above and in the referenced patents). Step 110 includes providing and positioning a compressible/expandable bladder over the plate magnetostrictive sensor probe structure. This compressible/expandable bladder may be any of a number of different types of structures that are closed (i.e., contain a gel, a liquid, or a gas material) that maintains an outward response pressure when compressed by external forces. Alternately, the bladder may include inlet ports and outlet ports to increase the internal pressure or decrease the pressure as necessary to vary the force and compliance function of the bladder.

At Step 112 the method continues by providing and positioning a rigid inverted U-shaped frame over the compressible/expandable bladder and the associated plate magnetostrictive sensor probe. This specifically structured U-shaped frame follows the contours of the plate magnetostrictive sensor probe and hold the compressible/expandable bladder against the probe. In this manner, the bladder directs a force away from the frame towards the external surface of the pipe under investigation and holds the probe in place in the process.

Finally, in order to maintain the entire assembly of the present invention in place on the external surface of the pipe, at Step 114 a belt is positioned and tensioned around the pipe and the sensor frame to bring the probe assembly firmly against the pipe surface. Once again the resiliency of the compressible/expandable bladder serves to maintain an appropriate contact force on the plate magnetostrictive sensor probe without damaging it through over tensioning. The magnetostrictive sensor probe is then connected at Step 116 to the appropriate magnetostrictive sensor instrumentation and the system generates and receives interrogation signals into and from the pipe under investigation.

Although the present invention has been described in terms of the foregoing preferred embodiments, this description has been provided by way of explanation only and is not intended to be construed as a limitation of the invention. Those skilled in the art will recognize modifications of the present invention and its methods of use that might accommodate specific cylindrical pipe or tube structures and even specific sensor configurations. Such modifications as to pipe structures or sensor structures where such modifications are merely incidental to the specific NDE environment do not necessarily depart from the spirit and scope of the underlying invention.

We claim:

1. An apparatus for long-range torsional guided-wave inspection of piping through partial excitation and detection around a pipe circumference, the apparatus comprising:
   a plate magnetostrictive sensor probe;
   a frame for positioning the plate magnetostrictive sensor probe against an external surface of the pipe;
   a compressible/expandable bladder positioned between the frame and the plate magnetostrictive sensor probe in a manner that directs the magnetostrictive sensor probe against the external surface of the pipe; and
   a belt positioned around a circumference of the pipe across the frame in a manner that pulls the frame and the associated bladder and plate magnetostrictive sensor probe against the external surface of the pipe.

2. The apparatus of claim 1 wherein the plate magnetostrictive sensor probe is curved to approximate the curvature of the pipe circumference.

3. The apparatus of claim 1 further comprising a strip of magnetostrictive material positioned between the plate magnetostrictive sensor probe and the external surface of the pipe.

4. The apparatus of claim 3 further comprising a pad positioned between the magnetostrictive strip and the plate magnetostrictive sensor probe.

5. The apparatus of claim 3 wherein the strip of magnetostrictive material comprises a strip having a width incrementally larger than a width of the plate magnetostrictive sensor probe and a length the shorter of one-half the pipe circumference or four times the wavelength of the torsional guided-wave used for the inspection.

6. The apparatus of claim 1 wherein the frame comprises an inverted U-shaped structure having a plurality of frame feet, wherein the frame feet are structured for direct contact with the external surface of the pipe and function to limit the extent to which the frame may be drawn against the pipe.

7. The apparatus of claim 6 wherein the frame feet each comprise angled base surfaces contoured to follow the curvature of the external surface of the pipe under inspection.

8. The apparatus of claim 1 wherein the compressible/expandable bladder comprises a closed cell having a flexible wall and containing a partially compressible material.

9. The apparatus of claim 1 wherein the compressible/expandable bladder comprises a closed cell having at least one port for introducing a fluid into, or removing a fluid from the cell, so as to increase or decrease a fluid pressure within the cell and thereby increase or decrease a force against the plate magnetostrictive sensor probe against the external surface of the pipe.

10. The apparatus of claim 1 further comprising a belt tensioner for tightening the belt around the pipe and across the frame to facilitate securing the plate magnetostrictive sensor probe against the external surface of the pipe.

11. A method for inspecting pipe with limited access using a partial excitation/detection apparatus positioned around the pipe circumference, the method comprising the steps of:
   providing and positioning a curved plate magnetostrictive sensor probe over the external surface of the pipe along a portion of a circumference of the pipe;
   providing and positioning a compressible/expandable bladder over the curved plate magnetostrictive sensor probe;
   providing and positioning a rigid inverted U-shaped frame over the compressible/expandable bladder and plate magnetostrictive sensor probe; and
   connecting the magnetostrictive sensor probe to magnetostrictive sensor instrumentation and generating and receiving interrogation signals into and from the pipe under inspection.

12. The method of claim 11 further comprising the steps of:
   establishing the length of a magnetostrictive strip to be placed on the pipe circumference as the shorter of one-half the pipe circumference or four times the torsional wave wavelength (T) used with the inspection;

providing a strip of magnetostrictive material having the established length for placement on the pipe circumference;

adhering the magnetostrictive strip along the circumference of the pipe on the external surface of the pipe; and positioning the curved plate magnetostrictive sensor probe over the magnetostrictive strip on the pipe surface.

13. The method of claim 12 wherein the step of providing a strip of magnetostrictive material comprises providing a magnetostrictive strip magnetized along the length of the strip to establish a bias magnetic field to optimize torsional wave magnetostrictive sensor operation.

14. The method of claim 11 further comprising the steps of:

providing and positioning a belt around the pipe and U-shaped frame to bring the probe assembly against the pipe surface; and tensioning the belt to secure the magnetostrictive sensor probe assembly against the external surface of the pipe.

15. A method for inspecting pipe with limited access using a partial excitation/detection apparatus positioned around the pipe circumference, the method comprising the steps of:

establishing the length of a magnetostrictive strip to be placed on the pipe circumference as the shorter of one-half the pipe circumference or four times the torsional wave wavelength (T) used with the inspection;

providing a strip of magnetostrictive material having the established length for placement on the pipe circumference, the magnetostrictive strip magnetized along the length of the strip to establish a bias magnetic field to optimize torsional wave magnetostrictive sensor operation;

adhering the magnetostrictive strip along the circumference of the pipe on the external surface of the pipe;

providing and positioning a curved plate magnetostrictive sensor probe over the magnetostrictive strip on the pipe surface;

providing and positioning a compressible/expandable bladder over the curved plate magnetostrictive sensor probe;

providing and positioning a rigid inverted U-shaped frame over the compressible/expandable bladder and plate magnetostrictive sensor probe;

providing and positioning a belt around the pipe and U-shaped frame to bring the probe assembly against the pipe surface;

tensioning the belt to secure the magnetostrictive sensor probe assembly against the external surface of the pipe; and connecting the magnetostrictive sensor probe to magnetostrictive sensor instrumentation and generating and receiving interrogation signals into and from the pipe under inspection.

\* \* \* \* \*